United States Patent
Soto

(10) Patent No.: US 7,097,852 B1
(45) Date of Patent: Aug. 29, 2006

(54) SOLUTION COMPRISING SEA WATER AS EXPECTORANT AND VIRUCIDAL FOR THE TREATMENT OF RESPIRATORY DISEASES AND METHOD TO USE AND DEVELOP

(76) Inventor: Jose A. Soto, 8935 Garland Ave., Surfside, FL (US) 33154

( * ) Notice: Subject to any disclaimer, the term of this patent is extended or adjusted under 35 U.S.C. 154(b) by 421 days.

(21) Appl. No.: 10/641,704

(22) Filed: Aug. 18, 2003

Related U.S. Application Data

(63) Continuation-in-part of application No. 10/431,721, filed on May 9, 2003.

(51) Int. Cl.
  *A61K 9/00* (2006.01)
  *A61K 9/08* (2006.01)
  *A61K 9/12* (2006.01)

(52) U.S. Cl. .............. 424/439; 424/455; 424/45; 424/680; 210/652

(58) Field of Classification Search .......... 424/45, 424/680, 677, 439, 455; 514/826, 855; 210/652
See application file for complete search history.

(56) References Cited

U.S. PATENT DOCUMENTS

| 4,822,512 | A | 4/1989 | Auchincloss | 252/106 |
| 6,451,352 | B1 * | 9/2002 | Yvin et al. | 424/680 |
| 6,508,936 | B1 * | 1/2003 | Hassan | 210/652 |
| 6,534,075 | B1 | 3/2003 | Hei et al. | 424/405 |
| 2003/0205526 | A1 * | 11/2003 | Vuong | 210/652 |

OTHER PUBLICATIONS

U.S. Appl. No. 10/431,721, filed May 9, 2003, Soto, Jose A.

* cited by examiner

*Primary Examiner*—Johann Richter
*Assistant Examiner*—Mina Haghighatian
(74) *Attorney, Agent, or Firm*—Sanchelima & Assoc., P.A.

(57) ABSTRACT

A solution comprised filtered natural sea water comprising pharmaceutically active salts and trace elements having a direct effect in the respiratory tissues and secretions as expectorant, mucolytic, decongestant and virucidal. Aerosolized treatments of the solution for a patient in need thereof dehydrates tissue, destroys mucous plugs, and mobilizes phlegm in the respiratory tract. A method of preparing the solution, comprises extracting seawater from a depth beyond where microscopic organism known as plankton lives, in an ocean; filtering said seawater to obtain desired concentration of elements; testing said seawater for microbiological and chemical analysis; and preparing the solution for packaging, having a predetermined approximated seawater element content as expectorant, mucolytic, decongestant, and virucidal.

6 Claims, No Drawings

SOLUTION COMPRISING SEA WATER AS EXPECTORANT AND VIRUCIDAL FOR THE TREATMENT OF RESPIRATORY DISEASES AND METHOD TO USE AND DEVELOP

OTHER RELATED APPLICATIONS

The present application is a continuation-in-part of pending of U.S. patent application Ser. No. 10/431,721, filed on May 9, 2003, which is hereby incorporated by reference.

BACKGROUND OF THE INVENTION

1. Field of the Invention

The present invention relates to the use of a solution as expectorant and decongestant, and more particularly, to the use of the solution made of filtered natural sea water comprising pharmaceutically active salts and trace elements having a direct effect in the respiratory tissues and secretions as expectorant, mucolytic, decongestant and virucidal.

2. Description of the Related Art.

Research on the above referenced have been published in the following:

Betakova, T. and Moss, B.; *Disulfide Bond and Membrane Topology of the Vaccinia Virus A17L Envelope Protein*, March 2000. Journal of Virology. Vol. 74, No.5, p. 2438–2442.

St J Jones, P; Korte, T and Blumenthal, R; *Conformational Changes in Cell Surface HIV-1 Envelope Glycoproteins are Triggered by Cooperation between Cell Surface CD4 and Co-receptors*. 1998; J. Bio I. C. 273: 404–409.

Tuma R, Bamford JH, Bamford DR, et al; *Structure, Interactions and Dynamics of PDR1 virus II. Organization of the Viral Membrane and DNA*. 1996; Journal of Molecular Biology. March 22; 257 (1): 102–15

Applicant believes that the closest reference corresponds to applicant's own patent application. The present application, however, includes subject matter not disclosed in the parent application, particularly, since the use of a solution made of filtered natural sea water comprising pharmaceutically active salts and trace elements is claimed, wherein the solution has a direct effect in respiratory tissues and secretions as expectorant, mucolytic, decongestant, and virucidal.

Applicant believes that a close reference corresponds to U.S. Pat. No. 4,822,512 issued to Auchincloss for Biocidal, particularly virucidal, compositions. However, it differs from the present invention because Auchincloss teaches a dry, water-soluble biocidal composition comprising (a) 0.01 to 5 parts by weight of water-soluble inorganic halide, (b) 25 to 60 parts by weight of an oxidizing agent which, in aqueous solution, reacts with the halide to generate hypohalite ions, (c) 3 to 8 parts by weight of sulfamic acid, (d) 0 to 20 parts by weight of a non-reducing organic acid, (e) 10 to 30 parts by weight of an anhydrous alkali metal phosphate, the parts by weight of the composition totaling 100, the pH of a 1% by weight aqueous solution of the composition being between 1.2 and 5.5, and the composition being characterized by lack of evolution of halogen at a pH less than 3.0 and a biocidal activity substantially greater than that produced by like compositions having inorganic halide concentrations greater than about 20%.

Furthermore, Auchincloss teaches the use of biocidal and virucidal compositions that could be used safely on farm animals. The composition benefits include that it is non-corrosive, non-irritant to the skin or eyes in its aqueous form, and it can be sprayed in rooms without discomfort. The composition solvent includes sea water. In addition, the composition comprises sodium chloride, potassium persulfate and sulfunate, which produce virucidal activity. However, the composition's pH is extremely acidic and it is used to spray livestock buildings, calves, piglets and horses.

Clinical examination of the skin and mucous membranes of the livestock established no inflammatory or any other adverse response on the part of the animals.

Animal viruses can be divided into two major categories, naked viruses and enveloped viruses.

Naked viruses contain only ribonucleic acids "RNA" or deoxyribonucleic acids "DNA" and a protein coat. Enveloped viruses also contain RNA or DNA plus a protein coat, and a lipid containing membrane, also called envelope. The naked and enveloped viruses are intracellular obligated parasites. However, to cause infection of other cells, they may be exposed to the environment or surrounding tissues. This phase is called the infectious phase.

Known prior art shows that proteins and lipids, which are stabilized by disulfide chemical bonds, form viral membrane. Membrane components such as hemagglutinins are anchored to the viral membrane by hydrophobic bonds. The membrane structure is held together by both types of chemical links, covalent and non covalent bonds. During viral infections, the viruses penetrate the cells through a mechanism defined as fusion. This is a form of viral penetration through the cellular walls, into the cytoplasm of the cell, and it requires a low acid pH.

Applicant believes that another close reference corresponds to U.S. Pat. No. 6,534,075 issued to Hei, et al. for Antimicrobial and antiviral compositions and treatments for food surfaces. However, it differs from the present invention because Hei, et al. teaches an antimicrobial and antiviral composition in powder form or in the form of a two part liquid concentrate for washing and sanitizing foods, food surfaces, food ware, process waters, animal quarters, and animal carcasses. The composition may also be used to reduce the microbial and viral population on animals; reducing human pathogenic microbes, reducing opportunistic pathogenic microbes on eggs, and treating skin diseases. The composition includes three reactive species, which in solution form an oxidizing species, and optionally a food grade acid source. The reactive species include a natural source of a quaternary or protonizable nitrogen compound, which is acceptable on foods, an oxidant and a halide source.

Other patents describing the closest subject matter provide for a number of more or less complicated features that fail to solve the problem in an efficient and economical way. None of these patents suggest the novel features of the present invention.

SUMMARY OF THE INVENTION

A therapeutic solution comprised of filtered seawater and firstly administered in the form of an aerosolized solution in the respiratory tract of mammals. The therapeutic solution has a direct effect in respiratory tissues and secretions as expectorant, mucolytic, decongestant and virucidal.

The therapeutic solution is further characterized in that the filtered seawater comprises a mixture of cations selected from the group consisting of sodium, magnesium, calcium and potassium, and anions selected from the group consisting of chloride, and sulfate.

The therapeutic solution is further characterized in that the filtered seawater comprises approximately 277.00–555.00 millimoles per liter sodium, 417.00–894.00 millimoles per liter chloride, 9.80–11.70 millimoles per liter potassium, 20.90–26.13 millimoles per liter sulfate, 45.60–60.49 millimoles per liter magnesium, and 8.11–10.87 millimoles per liter calcium, wherein osmolality is 920 to 1,130 mOsml/Kg and pH is 5.7–6.8.

The therapeutic solution is further characterized in that the filtered seawater comprises trace elements and a therapeutic solvent. The therapeutic solvent is the seawater.

The therapeutic solution is further characterized in that the therapeutic solution is firstly administered by aerosol to the respiratory tract of the mammals such that the therapeutic solution contacts areas where the mucosa secretions accumulate including nose, pharynx, larynx, trachea, bronchi, bronchioles and alveoli.

The therapeutic solution is further characterized in that the therapeutic solution is secondly administered by nebulization with a dose of approximately between one to ten ml via nasal or oral cavity to reach intratracheobronchial tissues and secretions, with a varying frequency of administration according the mammals age group and clinical diagnosis. The nebulization every two to twelve hours and extending three to fifteen minutes. The therapeutic solution may be thirdly administered in a dry form through inhalations of one to three per time.

The therapeutic solution is further characterized in that the therapeutic solution is fourthly administered with tents and/or a vaporization system in a continuous form for up to twenty-four hours or more.

The instant invention is also a method of affecting respiratory tissues and secretions as expectorant, mucolytic, decongestant and virucidal in a mammal in need thereof, comprising administering to the mammal an effective amount of a therapeutic solution. The therapeutic solution is comprised of filtered seawater and firstly administered in the form of an aerosolized solution.

The method also includes the therapeutic solution firstly administered as an aerosolized solution via nasal or oral cavity to reach intratracheobronchial tissues and the secretions.

The method also includes the therapeutic solution increases the solubility and volume of the phlegm in a respiratory tract reducing the adhesiveness and making them easier to expel by means of coughing or suctioning, providing a symptomatic relief of cough and congestion associated with the bronchial asthma, acute and chronic bronchitis, and common colds.

The method also includes the therapeutic solution increases output of the secretions from the respiratory tract by stimulating ciliary movement, which facilitate the removal of mucus.

The method also includes the therapeutic solution stimulates water transport into an airway lumen to decrease the inflammatory changes in a respiratory tree associated with bronchial asthma, acute and chronic bronchitis, and common colds.

The method also includes the therapeutic solution is secondly administered by nebulization with a dose of approximately between one to ten ml of via nasal or oral cavity to reach intratracheobronchial tissues and the secretions with a varying frequency of administration according to the mammals age group and clinical diagnosis. Nebulizations every two to twelve hours and extending three to fifteen minutes.

The instant invention is also a method of preparing a therapeutic solution, comprising:

A) extracting seawater from a depth beyond where microscopic organism known as plankton lives, in an ocean;

B) filtering said seawater to obtain desired concentration of elements, said elements primarily comprising sodium, magnesium, calcium, potassium, chloride, and sulfate;

C) testing said seawater for microbiological and chemical analysis; and

D) preparing a solution for packaging, having a predetermined approximated seawater element content as expectorant, mucolytic, decongestant, and virucidal.

It is therefore one of the main objects of the present invention to provide a solution made of filtered natural sea water comprising pharmaceutically active salts and trace elements that have a direct effect in respiratory tissues and secretions when administered.

It is another object of this invention to provide a solution made of filtered natural sea water comprising pharmaceutically active salts and trace elements that are expectorant, mucolytic, decongestant and have a virucidal effect when administered.

It is another object of the present invention to provide a solution made of filtered natural sea water comprising pharmaceutically active salts and trace elements, for solution aerosol administration in the form of vials.

It is yet another object of the present invention to provide a solution having a low acid pH that allows viral penetration through cellular walls, into the cytoplasm of a cell.

It is still another object of this invention to provide such a solution that is inexpensive to manufacture and administer while retaining its effectiveness.

Further objects of the invention will be brought out in the following part of the specification, wherein detailed description is for the purpose of fully disclosing the invention without placing limitations thereon.

DETAILED DESCRIPTION OF THE PREFERRED EMBODIMENT

Seawater is processed to obtain pharmacologically active solutions for the treatment of respiratory diseases.

The solution of the instant invention is administered to mammals for the intratracheobronchial treatment of respiratory illnesses in the form of nebulizations. The solution is placed in a plastic receptacle or alike, to be delivered into the respiratory system organs using a pressure gradient to transport the solution and its active ingredients in a gaseous form.

The solution is administered into the tracheobronchial tract through the nasal or oral cavity and the power source necessary to introduce the preparation may be breathed air (inhalation) of a patient himself or a power source other than the breathed air of the patient, such as, but not limited to, a balloon method, air compressor, ultrasonic systems or alike.

The doses and frequency of the treatments may vary according with the diagnosis and the patients' age. The usual dose of a nebulization may be between 1 to 10 ml of the solution via nasal or oral cavity to reach the intratracheobronchial tissues and secretions. In a dry form, administration may be through inhalations/puffs of one to three per time. The frequency of administration may change as well according with the patient age group and the clinical diagnosis. One nebulization every 2 to 8 hours is usual. The typical time expended on each nebulization is between 3 to 15 minutes.

Aerosol treatments can be given also using tents and/or a vaporization system to create the desired effect. In these cases, the time of vaporization may be twenty-four hours or more.

The aerosols have an expectorant effect by humidification of tenacious sputum accumulated in the respiratory organs.

Small drops delivered directly into the tissues where the respiratory secretions accumulate, change their chemical constitution and physical shape to a more liquid form easier to expel out of the respiratory tree.

Without being bound by any theory, the present inventor believes that the solution has a direct effect in respiratory tissues and secretions as expectorant, mucolytic, decongestant and virucidal.

The solution and/or its variants may be used as a vehicle for other drugs to be delivered into the respiratory tract of a mammal. This adds a synergistic effect to different medications used for the treatment of respiratory problems such as bronchial asthma, acute and chronic bronchitis and common colds. Properties of the solution include anti-inflammatory, mucolytic, decongestant, expectorant and virucidal. These properties add a therapeutic effect to the patient when combined with other drugs and administered via aerosol. The use of this solution as a vehicle in any form or concentration makes administered medication more effective, since the key elements dissolved in their natural form, sea water, remain in constant proportions.

Without being bound by any theory, the present inventor believes that another condition that can be treated with the claimed invention is chronic obstructive pulmonary disease, better known as "COPD". COPD comprises a group of symptoms and clinical signs caused by several diseases. The diseases include two major entities defined as: chronic bronchitis and pulmonary emphysema. In addition, a third entity includes bronchiectasis.

Although there is a common clinical and pathological ground for these type of respiratory disorders, pulmonary emphysema is characterized by alveolar septum destruction and periods of exacerbation. Symptoms of pulmonary emphysema include cough, sputum production, shortness of breath, and the presence of pulmonary sepsis.

Bronchiectasis is a terminology reserved for cases of extreme bronchial dilatation and secondary infection characterized by thick sputum production and cough. Brochiectasis can occur as a complication of emphysema, bronchitis or other pulmonary problems. In addition, genetical forms of brochiectasis have been analyzed.

All the above conditions have symptoms that improve with the use of the solution. Additionally, outcomes of preliminary studies indicate that the solution has a mucolytic effect on the sputum, changing its chemical and physical composition, which allows the patient an easier way to expel it from respiratory tissues.

Without being bound by any theory, the present inventor believes that the solution has an antiviral effect causing the death of viruses in respiratory infections, during the infectious phase of their cycle.

The present invention also includes a method of treatment using the solution to inhibit and destroy enveloped respiratory viruses through an effect of a direct action on the viral coating structures. This is the lipid containing membrane called envelope and the protein coat. The slightly acid pH of the solution made from sea water allows a chemical reaction of the pharmacologically active salts with the disulfide bonds that normally stabilize membrane structures. As a result, a cleavage occurs and the viral permeability is altered. The virus becomes osmotically fragile. Additional conformational changes occur and provoke a fusion like stage, as a result of these reactions on the membrane and the protein coat, the nucleic acids are exposed and subsequently destroyed.

The solution also has a virucidal effect over naked viruses, viruses containing only ribonucleic acid or deoxyribonucleic acid and a protein coat. Once the solution low pH and its pharmacologically active salts, in reaction with the disulfide bonds, induce the conformational changes, the nucleic acids are exposed. Hydrogen bonds between the bases that hold together the two strands of nucleotide, react with the pharmacological salts that conform the active ingredients of the solution. This allows the separation of the strands, this is the thermodynamic reaction. The final result is the direct elimination of the viruses by a detergent like effect. The inhibition of the virus's pathogenicity causes a significant improvement and symptoms relief of the mammals suffering from viral respiratory infections.

Without being bound by any theory, the present inventor also believes that the solution has a therapeutic effect against viruses affecting the respiratory tract of mammals, particularly in those affected by respiratory diseases where this viruses can cause severe damaged. This includes, but is not limited to asthma, acute bronchitis, chronic obstructive pulmonary disease and common colds. The solution also has a prophylactic effect against viral infections in mammals receiving its aerosolized form.

The solution may be administered for a virucidal effect in a dry form as well as using an aerosol system to deliver the active salts into the respiratory tract. The solution obtains a desired action over respiratory viruses and is tolerable for mammals' respiratory tissues.

In the preferred embodiment, the instant invention is a solution having pharmacological compositions containing the elements seen in Chart 1 below or the pharmacologically acceptable salts thereof, for aerosol administration in the form of vials.

Examples of the solution packaging according to the invention are:

i) vials containing 1 to 30 ml of the solution for aerosol administration; and ii) multi-dose containers carrying 50 to 1000 ml of the solution for aerosol administration.

The present invention also includes a method of preparing a solution, comprising:

A) extracting seawater from a depth beyond where microscopic organism known as plankton lives, in an ocean;

B) filtering said seawater to obtain desired concentration of elements, said elements primarily comprising sodium, magnesium, calcium, potassium, chloride, and sulfate;

C) testing said seawater for microbiological and chemical analysis; and

D) preparing a solution for packaging, having a predetermined approximated seawater element content as expectorant, mucolytic, decongestant, and virucidal.

Step A) of the method includes, extracting seawater from a depth beyond where microscopic organism known as plankton lives, in an ocean. Typically, the depth beyond where the plankton lives is seven meters. In the preferred embodiment, the extraction is done in an area exposed to open ocean.

Step B) of the method includes, filtering said seawater to obtain the desired concentration of elements, said elements primarily comprising sodium, magnesium, calcium, potassium, chloride, and sulfate. The seawater is filtered using a density filter for a decantation process using a multilayer cellulose filter to remove undesired particles and to obtain the desired solution concentration. In the preferred embodiment, only two layers of cellulose filters are utilized for the decantation process to obtain a more natural concentration of salts.

Step C) of the method includes, testing said seawater for microbiological and chemical analysis. The seawater is radiated using ultraviolet light to preserve its sterility. Solution samples are collected and tested for microbiological and chemical analysis. Once this process is concluded, the solution is stored in a metallic receptacle at a steady temperature. The resulting solution comprises a formulation of six key elements, making approximately ninety-nine percent of the dissolved solids: sodium, magnesium, calcium, potassium, chloride, and sulfate.

Step D) of the method includes, preparing a solution for packaging, having a predetermined approximated seawater element content as expectorant, mucolytic, decongestant, and virucidal. The packaging may be in the form of vials containing 1 to 30 ml of the solution for aerosol administration, and/or multi-dose containers carrying 50 to 1000 ml of the solution for aerosol administration. However, other containers housing the solution may be utilized for effective administration.

The specification of an example solution prepared according to the described method is seen in chart 1 below. It is noted that mmol/l is millimoles per liter. The elements listed are an average, and may fluctuate, as it is noted that they are derived from the ocean. However, it is noted that the result is a solution comprising a formulation of six key elements making ninety-nine percent of the dissolved solids.

CHART 1

|  | FROM mmol/L | TO mmol/L |
| --- | --- | --- |
| SODIUM | 277.00 | 555.00 |
| CHLORIDE | 417.00 | 894.00 |
| POTASSIUM | 9.80 | 11.70 |
| SULFATE | 20.90 | 26.13 |
| MAGNESIUM | 45.60 | 60.49 |
| CALCIUM | 8.11 | 10.87 |
| Osmolality: 920 to 1130 mOsml/Kg |  |  |
| pH 5.7 to 6.8. |  |  |

The solution of Chart 1 may additionally contain natural trace elements, as seen in Chart 2 below, of significant amounts approximating:

CHART 2

|  | mg/l |
| --- | --- |
| CARBON | 28.0 |
| BROMINE | 67.0 |
| STRONTIUM | 8.0 |
| FLUORIDE | 1.3 |
| IODINE | 0.06 |
| LITHIUM | 0.18 |
| RUBIDIUM | 0.12 |
| NITROGEN | 11.5 |
| PHOSPHORUS | 0.06 |
| SILICON | 2.0 |
| ARGON | 0.43 |
| BARIUM | 0.02 |
| MOLYBDENUM | 0.01 |
| BORON | 4.4 |

Furthermore, the solution of Chart 2 may additionally contain smaller amounts of natural trace elements, as seen in Chart 3 below, approximating:

CHART 3

|  | mg/l |  | mg/l |
| --- | --- | --- | --- |
| URANIUM | 0.0032 | NEON | 0.00012 |
| VANADIUM | 0.0025 | MANGANESE | 0.0001 |
| TITANIUM | 0.001 | CADMIUM | 0.0001 |
| ZINC | 0.0005 | COPPER | 0.0001 |
| NICKEL | 0.00048 | TUNGSTEN | 0.0001 |
| ALUMINUM | 0.0004 | IRON | 0.000055 |
| CESIUM | 0.0004 | XENON | 0.00005 |
| CHROMIUM | 0.0003 | ZIRCONIUM | 0.00003 |
| ANTIMONY | 0.00024 | BISMUTH | 0.00002 |
| KRYPTON | 0.0002 | NIOBIUM | 0.00001 |
| SELENIUM | 0.0002 | THALLIUM | 0.00001 |

The presence of trace elements, seen in Charts 2 and 3, although not part of the key components, is considered essential for the solution because they are part of the compound as a whole in the form of pharmacologically stable salts or isolated elements. Thus having beneficial effects as part of the medical treatments.

The type of the trace elements will vary with the seawater origin, so may its concentration. The solvent for the solution is the seawater. The compounds of the invention, as well as the pharmaceutically acceptable salts thereof, due to the pharmacological properties and very low toxicity can be used as active ingredients for the preparation of medicaments for the respiratory diseases.

After testing the solution in human volunteers, it showed not to be irritant to the mucosa of the respiratory tree, mouth or the eye tissues. The compound was well tolerated in its aerosol protocol.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A therapeutic solution comprised of filtered seawater in the form of an aerosolized solution in the respiratory tract of mammals, said therapeutic solution having a direct effect in respiratory tissues and secretions as expectorant, mucolytic and decongestant wherein said filtered seawater comprises approximately from 277.00 to 555.00 millimoles per liter of sodium, 417.00 to 894.00 millimoles per liter of chloride, 9.80 to 11.70 millimoles per liter of potassium, 20.90 to 26.13 millimoles per liter of sulfate, 45.60 to 60.49 millimoles per liter of magnesium, and 8.11 to 10.87 millimoles per liter of calcium, wherein osmolality is from 920 to 1,130 mOsml/Kg and pH is between 5.7 and 6.8.

2. The therapeutic solution set forth in claim 1, further characterized in that said therapeutic solution is administered by aerosol to said respiratory tract of said mammals such that said therapeutic solution contacts areas where said mucosa secretions accumulate including nose, pharynx, larynx, trachea, bronchi, bronchioles and alveoli.

3. The therapeutic solution set forth in claim 2, further characterized in that said therapeutic solution is administered by nebulization with a dose of approximately between one to ten ml via nasal or oral cavity to reach intratracheobronchial tissues and secretions with a varying frequency of administration according to said mammals age group and clinical diagnosis, said nebulization every two to twelve hours and extending three to fifteen minutes, said therapeutic solution may be administered in a dry form through inhalations of one to three per time.

4. The therapeutic solution set forth in claim 2, further characterized in that said therapeutic solution is administered with tents or a vaporization system in a continuous form for up to twenty-four hours.

5. A method for treating respiratory tissues and secretions as expectorant, mucolytic and decongestant in a mammal in need thereof, comprising administering to said mammal an effective amount of a therapeutic solution as set forth in claim 1, said therapeutic solution comprised of filtered seawater and administered in the form of an aerosolized solution via nasal or oral cavity by nebulization with a dose of approximately between one to ten ml. with varying frequency of administration according to said mammal's age group and clinical diagnosis, said nebulization administered every two to twelve hours, extending three to fifteen minutes to reach intratracheobronchial tissues and secretions and said solution increases the solubility and volume of the phlegm in a respiratory tract reducing the adhesiveness and making them easier to expel by means of coughing or suctioning, providing a symptomatic relief of cough and congestion associated with bronchial asthma, acute and chronic bronchitis and common colds, and wherein said solution increases output of said secretions from said respiratory tract by stimulating ciliary movement which facilitates the removal of mucus and said solution stimulates water transport into an airway lumen to decrease the inflammatory changes in a respiratory tree associated with bronchial asthma, chronic bronchitis and common colds.

6. The solution set forth in claim 2 wherein said solution is used as a vehicle for delivering drugs into the respiratory tract of a mammal.

* * * * *